United States Patent
Wu et al.

(10) Patent No.: US 6,413,215 B1
(45) Date of Patent: Jul. 2, 2002

(54) IMPLANT WEAR DEBRIS DETECTION APPARATUS AND METHOD

(75) Inventors: Junru Wu, S. Burlington, VT (US); Eric M. Weissman, Chagrin Falls; Elmer D. Dickens, Jr., Richfield, both of OH (US)

(73) Assignee: The University of Vermont, Burlington, VT (US)

( * ) Notice: Subject to any disclaimer, the term of this patent is extended or adjusted under 35 U.S.C. 154(b) by 40 days.

(21) Appl. No.: 09/660,639

(22) Filed: Sep. 13, 2000

Related U.S. Application Data (60) Provisional application No. 60/194,996, filed on Apr. 5, 2000.

(51) Int. Cl.$^7$ ................................. A61B 8/00
(52) U.S. Cl. ..................................... 600/437
(58) Field of Search ................. 600/437, 442, 600/438, 439, 443; 73/597

(56) References Cited

U.S. PATENT DOCUMENTS

| | | | |
|---|---|---|---|
| 5,143,069 A | | 9/1992 | Kwon et al. |
| 5,720,290 A | | 2/1998 | Buhler et al. |
| 5,725,597 A | | 3/1998 | Hwang |
| 5,749,362 A | * | 5/1998 | Funda et al. .................. 348/77 |
| 6,203,497 B1 | * | 3/2001 | Dekel et al. ................. 128/916 |
| 6,328,695 B1 | * | 12/2001 | Vammen et al. ............. 600/442 |

FOREIGN PATENT DOCUMENTS

| | | |
|---|---|---|
| EP | 0295521 | 12/1988 |
| WO | 9006720 | 6/1990 |

OTHER PUBLICATIONS

"Acoustic Microcavitation: its active and passive acoustic detection", pp. 1515–1523; Autor: Sameer I. Madanshetty, Sep. 1991 Acoustical Society of America.

"Mechanical Characterization of Microparticles by Scattered Ultrasound", Author: Ronalyd A Roy, et al; pp. 2332–2341; Jun. 1990 Acoustical Society of America.

"Polythethylene Wear and Synotitis in Total Hip Arthroplasty" The Journal of Arthroplasty, Feb. 1999, vol. 14, No. pp. 138–143.

"A Novel Method for Sub–Micron Particle Detection in Clean Liquids", by Sameer I. Madanshetty, IEEE Transons on Semiconductor Manufacturing, vol. 10, Feb. 1997, pp. 11–16.

"Technique for Identification of Submicron Metal Particulate From Implants in Histological Specimens", by Gregg A. Lundeen, et al.; Journal of Biomedical Materials Research, vol. 43, No. 2, 1998, pp. 168–174.

European Search Report regarding Application No. 1 PCT/US00/31818 dated Mar. 23, 2001.

\* cited by examiner

*Primary Examiner*—Francis J. Jaworski
*Assistant Examiner*—Maulin Patel
(74) *Attorney, Agent, or Firm*—Renner, Otto, Boisselle & Sklar, LLP (57) ABSTRACT

A system for detecting wear debris particulate from a medical implant within the body of a living animal is provided. The system includes an acoustic transmitter for transmitting acoustic energy from outside the body to a soft tissue region proximate the medical implant containing wear debris particles; an acoustic receiver located outside the body to detect resultant acoustic energy generated by the wear debris particles and produce a received signal indicative thereof; a processor for processing the received signal to evaluate at least one parameter associated with the wear debris particles; and an output for indicating the at least one parameter.

37 Claims, 5 Drawing Sheets

IMPLANT WEAR DEBRIS DETECTION APPARATUS AND METHOD

CROSS REFERENCE TO RELATED APPLICATION

This application claims priority under 35 USC §119 to U.S. provisional application No. 60/194,996, filed on Apr. 5, 2000.

TECHNICAL FIELD

The present invention relates generally to non-invasive diagnoses of medical implants, and more particularly to an ultrasound technique for the in-vivo detection of particulate wear debris from medical implants.

BACKGROUND OF THE INVENTION

Various types of medical implants have been developed over the years. In many instances, such implants enable humans to live longer, more comfortable lives. Implants such as pacemakers, artificial joints, valves, grafts, stents, etc. provide a patient with the opportunity to lead a normal life even in the face of major heart, reconstructive, or other type surgery, for example.

It has been found, however, that the introduction of such medical implants can sometimes lead to complications. For example, the human body may reject the implant which can ultimately lead to osteolysis or other types of complications. Alternatively, the implant may malfunction or become inoperative.

In the case of some implants such as artificial joints, the implant is subjected to everyday motion, stress and strain. This often leads to abrasion between different parts of the implant, between the implant and the skeletal frame, etc. Such abrasion results in the formation of wear debris particles in the area of the implant which can lead to complications. For example, in the case of an artificial hip joint, wear debris particles from the acetabular cup may build up over time. These wear debris particles can trigger a response of the human body immune system. Because the wear debris particles typically consist of artificial materials which are nonbiodegradable, the immune system attacks on the particles fail. This leads to further increases in immune system enzyme concentration and ultimately resorption of bone by the tissue, a process called osteolysis. The patient can experience a loose joint and pain.

It is desirable therefore to be able to monitor the condition of a medical implant, particularly in the case of an implant which is subject to the generation of wear debris particulate. On the other hand, it is highly undesirable to have to perform invasive surgery in order to evaluate the condition of the implant. Such invasive surgery is not only time consuming, but also costly and painful to the patient.

In view of the aforementioned shortcomings, there is a strong need in the art for an apparatus and method for detecting and evaluating wear debris particulate associated with a medical implant, particularly with respect to an artificial joint. Even more particularly, there is a strong need for an apparatus and method which can evaluate wear debris simply, reliably and non-invasively. Having the capability to detect such debris at an early enough stage would allow physicians to intervene with pharmaceuticals or otherwise before significant bone deterioration or other complications occur.

SUMMARY OF THE INVENTION

An apparatus and method are provided for the in-vivo detection of particulate wear debris from medical implants such as artificial joints for hips, knees, shoulders, elbows, etc. According to the invention, a focused ultrasound transducer placed in contact with the body insonifies a region of the body suspected of containing wear debris particulate. Such wear debris particulate may have linear dimensions on the order of 0.1 to 10 microns, for example. The particles are detected by the same or different transducer when cavitation events represented by bursts of scattered ultrasound with amplitudes orders of magnitude higher than background noise levels are received from the particles.

Applicants have found both a particle size and a concentration effect on the amplitude and number of the cavitation events. The cavitation events are believed to be linear and to result from small irregularities in the particle/liquid interface which trap microscopic volumes of gas that serve as cavitation nuclei. Computer analysis of the signal strength (i.e., amplitude) and number of cavitation events and the use of a lookup table or neural network, for example, provide a measurement of particulate distribution (size and concentration) in the vicinity of the implant.

According to the present invention, a system is provided for detecting wear debris particulate from a medical implant within a body of a living animal. The system includes an acoustic transmitter for transmitting acoustic energy from outside the body to a soft tissue region proximate the medical implant generating wear debris particles; an acoustic receiver located outside the body to detect resultant acoustic energy scattered by the wear debris particles and produce a received signal indicative thereof; a processor for processing the received signal to evaluate at least one parameter associated with the wear debris particles; and an output for indicating the at least one parameter.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENTS

The present invention will now be described with reference to the drawings, wherein like reference numerals are used to refer to like elements throughout.

Figure 1:
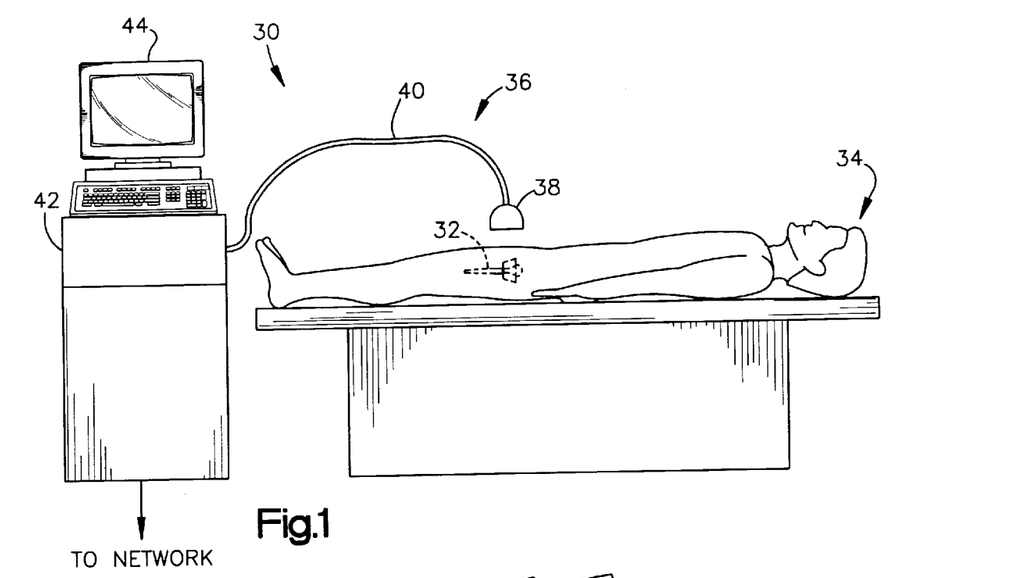
FIG. 1 is an environmental view illustrating a system for non-invasively detecting wear debris particulate associated with a medical implant, such as an artificial hip, in accordance with the present invention.

Referring initially to FIG. 1, a system for non-invasively detecting wear debris particulate from a medical implant is generally designated 30. In accordance with the present invention, the system 30 detects and analyzes wear debris particulate associated with a medical implant 32 which is implanted in a living animal such as a human patient 34. As is discussed in more detail below, the medical implant 32 can be any of a wide variety of different types of devices including, for example, an artificial joint, etc. In the preferred embodiment, the implant 32 is an artificial hip-joint, although it will be appreciated that the implant 32 can be any other type of device which is subject to the generation of wear debris particulate.

The system 30 includes an acoustic analyzer 36 for remotely and non-invasively analyzing the implant 32 in order to detect the presence of wear debris particulate (e.g., with respect to size and/or concentration). The analyzer 36 in the exemplary embodiment includes an acoustic transmitter/receiver unit 38 which is positioned outside the patient 34 in close proximity to the implant 32. As will be discussed in more detail below, the transmitter/receiver unit 38 serves to excite the soft tissue region around the implant 32 with acoustic energy. The acoustic energy is used to evaluate the response of the region suspected of containing wear debris particulate. In particular, the transmitter/receiver unit 38 receives acoustic signals radiated/scattered back by the region suspected of containing wear debris particulate in response to the excitation. Such signals are then processed by the analyzer 36 to detect a parameter of interest (e.g., particle concentration and/or size, etc.).

The transmitter/receiver unit 38 is coupled via an electrical cable 40 to the main circuitry 42 included in the analyzer 36. The main circuitry 42 includes suitable circuits for driving the transmitter/receiver unit 38 as described below, and for processing the output of the transmitter/receiver unit 38 in order to provide an output to an operator (e.g., via a display 44). In addition, or in the alternative, the output may be linked to a local area network (LAN), the Internet, etc., so that the results may be provided to a remote location if desired.

Figure 2:
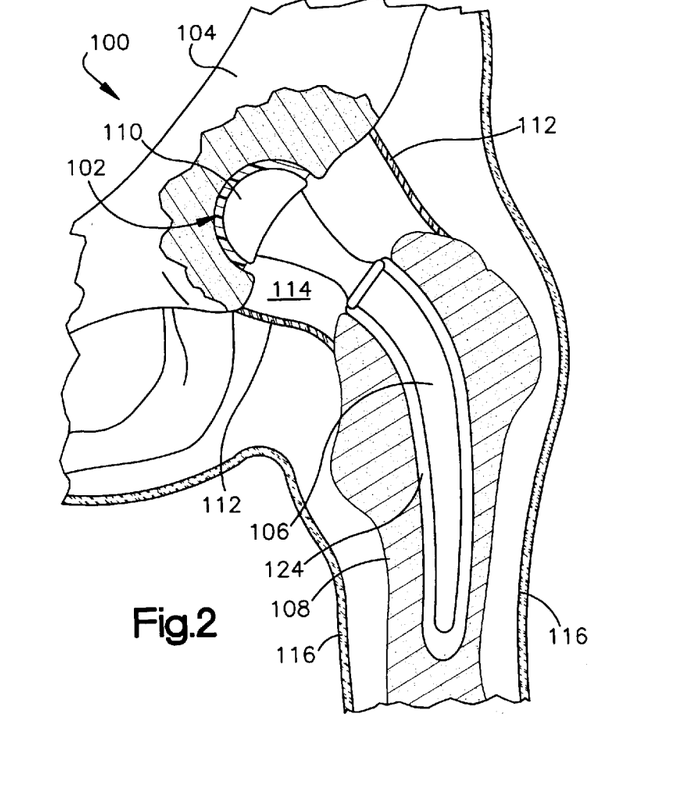
FIG. 2 is a sectional view illustrating an artificial hip-joint to be analyzed in accordance with the present invention.

FIG. 2 shows a typical artificial hip joint 100 which may be analyzed in accordance with the present invention. The hip joint 100 includes a hemispherical acetabular cup 102 implanted in the acetabulum of the pelvic bone 104. A shaft 106 is inserted into a space formed in the central portion of the femur 108 after removing the marrow existing in that portion of the femur 108. A spherical femur head 110 is fixed to an upper end of the shaft 106, and is pivotally fitted in the acetabular cup 102.

A soft tissue membrane forms a sack 112 which surrounds the joint 100 in the area where the femur head 110 is pivotally fitted in the acetabular cup 102. As is known, the sack 112 contains primarily synovial fluid 114 which serves to lubricate the joint 100. The joint is then surrounded by muscle tissue and skin as represented at 116.

A patient having an artificial hip joint 100 is typically able to walk in much the same manner as with a conventional hip. When the patient walks, the femur head 110 rotates and translates within the acetabular cup 102. During such movements, however, the femur head 110 generates interfacial friction with the acetabular cup 102 which is typically made of ultra-high molecular weight polyethylene or some other inert material. This results in an abrasion of the acetabular cup 102, and as a result fine polyethylene or other inert material wear debris particles are generated.

As is discussed below in relation to FIG. 3, these wear debris particles are contained within the sack 112 of synovial fluid 114. The particles are problematic in that they generate osteolysis by moving from the sack 112 into the space 124, for example. The abrasion of the acetabular cup 102 results in a reduction in the life of the joint 100. Moreover, gone unchecked the hip joint 100 may become dislocated due to excessive mobility in the shaft 106. Such dislocation causes the patient to feel pain. Furthermore, there is an increase in hospital expense. Additional details regarding a typical hip joint 100 and the associated wear particulate may be found in U.S. Pat. No. 5,725,597, the entire disclosure of which is incorporated herein by reference.

Figure 3:
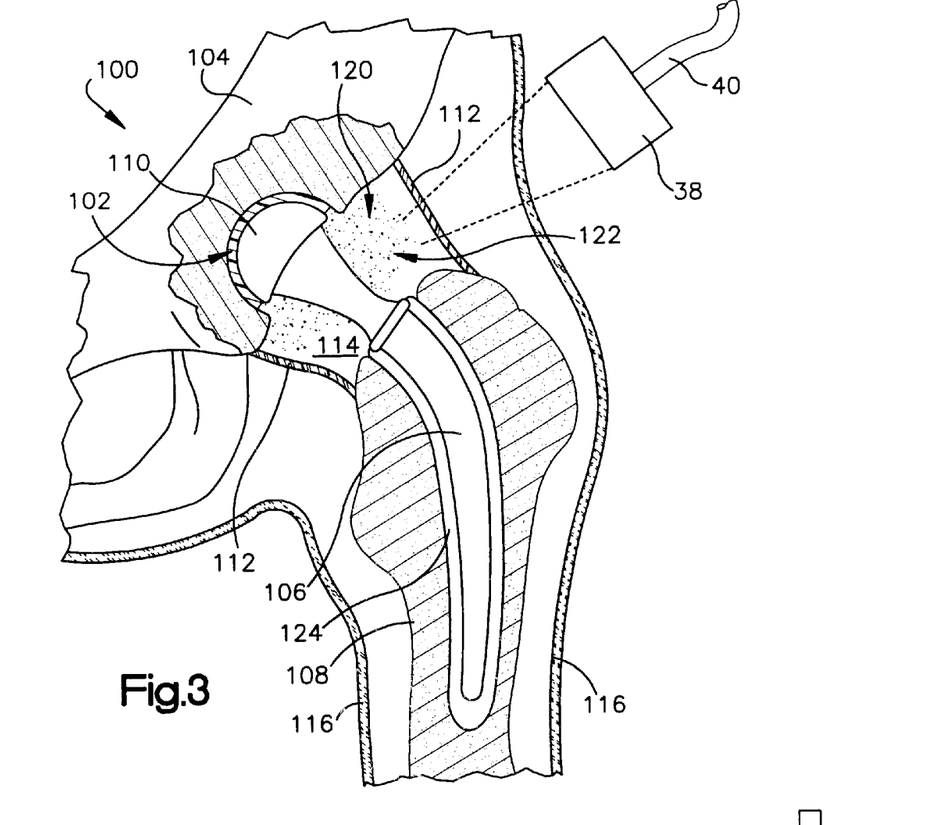
FIG. 3 is a sectional view of the artificial hip-joint of FIG. 2 including wear debris particulate to be analyzed in accordance with the present invention.

FIG. 3 represents the hip joint 100 after wear debris particulate 120 has built up in the synovial fluid 114. The wear debris particulate 120 may include particles of different sizes and concentrations, depending upon the materials used to manufacture the joint 100 and the extent of wear, for example. Typical particles 120 found in the synovial fluid 114 may range in size, for example, from 0.1 micron to 10 microns and higher with particles in the 0.4 to 1.0 micron range provoking the largest response from the immune system.

Accordingly, two objectives of the present invention are to detect the size and concentration of the particles in order to assess the integrity of the joint 100. For example, early detection of the presence and extent of wear debris particulate may allow for remedial action which is less costly, invasive, painful, etc. compared to allowing the buildup of particulate to continue undetected.

As shown in FIG. 3, the transmitter/receiver unit 38 is held against the body of the patient 34 in the vicinity of the hip joint 100. The transmitter/receiver unit 38 is designed to transmit excitation pulses of acoustic energy towards a region within the synovial fluid 114 within the sack 112. In between each excitation pulse, the transmitter/receiver unit 38 receives scattered bursts of acoustic energy which are created as a result of the excitation pulse generating cavitation events among the particulate 120 within the synovial fluid 114. The different amplitudes of the scattered bursts have been found to track the size of the different wear debris particles. In addition, the frequency or number of events (i.e., the number of scattered bursts detected in response to an excitation pulse) has been found to be indicative of the concentration of the wear debris particles. Accordingly, the present invention is able to detect and analyze the presence of wear debris particulate by analyzing the acoustic energy which is scattered back towards the transmitter/receiver unit 38 from the region containing the synovial fluid 114.

Figure 4:
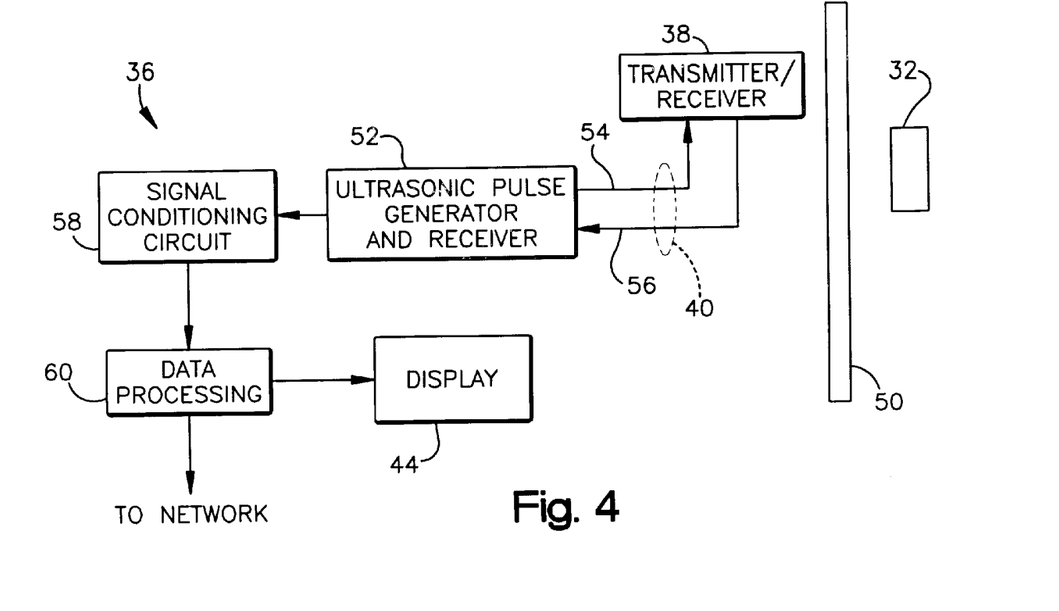
FIG. 4 is a block diagram of a wear debris detection system in accordance with the present invention.

Referring now to FIG. 4, the acoustic analyzer 36 in accordance with the exemplary embodiment is illustrated in more detail. The transmitter/receiver unit 38 preferably is a hand-held sized device which is held by a doctor, nurse or medical assistant against the body of the patient 34 in close proximity to the implant 32. The transmitter/receiver unit 38 may be a conventional single element or array type ultrasonic transducer used in medical or NDE applications as will be appreciated. It is understood that combinations of imaging transducers and single element transducers may be beneficial to the practice of this technology.

In this example, the implant 32 may be the artificial hip joint 100 of FIGS. 2 and 3. Since the system 30 is non-invasive, the transmitter/receiver unit 38 may be placed adjacent the implant 32 with the body of the patient (e.g., skin, muscle tissue, etc.), designated 50, disposed therebetween.

The analyzer 36 includes an ultrasonic pulse generator and receiver circuit 52 which is programmed to carry out the various control and functions described herein. More particularly, the ultrasonic pulse generator and receiver circuit 52 controls the frequency, the amplitude and the length of the ultrasonic pulses generated by the transmitter and also amplifies the received acoustic signals scattered back towards the transmitter/receiver unit 38 (e.g., from the particulate 120 within the synovial fluid 114) in response to being excited. The frequency can be changed between 0.1 MHz to 30 MHz, for example. The acoustic pressure amplitude can be changed between 0.05 Mpa to 3 Mpa, for example. The circuit 52 selectively provides a pulse control signal on bus 54 in order to control the frequency, amplitude, etc. of the acoustic energy the transmitter/receiver unit 38 transmits towards the implant 32. The acoustic energy is then scattered back towards the transmitter/receiver unit 38 (e.g., from the particulate 120 within the synovial fluid 114) in response to being excited by the excitation pulses.

The transmitter/receiver unit 38 receives acoustic energy scattered back from the wear debris particulate and converts the energy into an electrical signal on line 56. The signal on line 56 is received by circuit 52 and is input to a signal conditioning circuit 58 which conditions the received signal prior to being input to a data processing circuit 60. As is discussed more fully below, the data processing circuit 60 is programmed using conventional techniques to process and analyze the signal received on line 56 in order to determine a parameter(s) associated with the wear debris particulate. For example, the excitation signal from the transmitter/receiver unit 38 is used to create cavitation among the wear debris particles 120 within the synovial fluid 114. The transmitter/receiver unit 38 then detects the acoustic energy scattered back towards the transmitter/receiver unit 38 due to such cavitation. More specifically, the data processing circuit 60 analyzes the amplitude and frequency of the cavitation events, for example. As is pointed out below in connection with FIGS. 5–9, the amplitude of the cavitation events has been found to track the size of the particles, and the number of events has been found to track the concentration of the particles. The principles of cavitation are explained more fully in Madanshetty et al., *Acoustic Microcavitation: Its Active and Passive Acoustic Detection*, J. Acoust. Soc. Am., Vol. 90, 1515–1526, 1991, for example, the entire disclosure of which is incorporated herein by reference.

Figure 5:
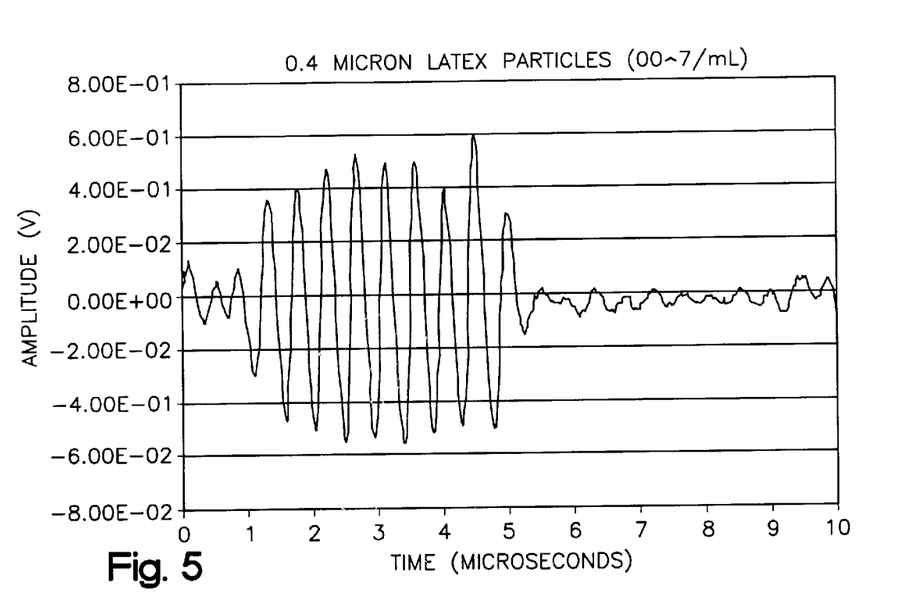
FIGS. 5, 6 and 7 represent data indicative of different particle sizes detected in accordance with the present invention.

FIG. 5 represents exemplary data showing the response of wear debris particulate having a diameter of 0.4 micron at a concentration of $10^7$ particles/milliliter(mL). In FIG. 5, a single event is shown in response to an excitation pulse from the transmitter/receiver unit 38 at a given amplitude within medically accepted practice and a frequency of 2.25 MHz. The circuit 52 captures the response signal received by the transmitter/receiver unit 38 representing a number of events, and the particular event shown in FIG. 5 may be selected via signal processing to partition the respective events. As is shown in FIG. 5, the amplitude of the response signal is approximately $5 \times 10^{-2}$ volts.

Figure 6:
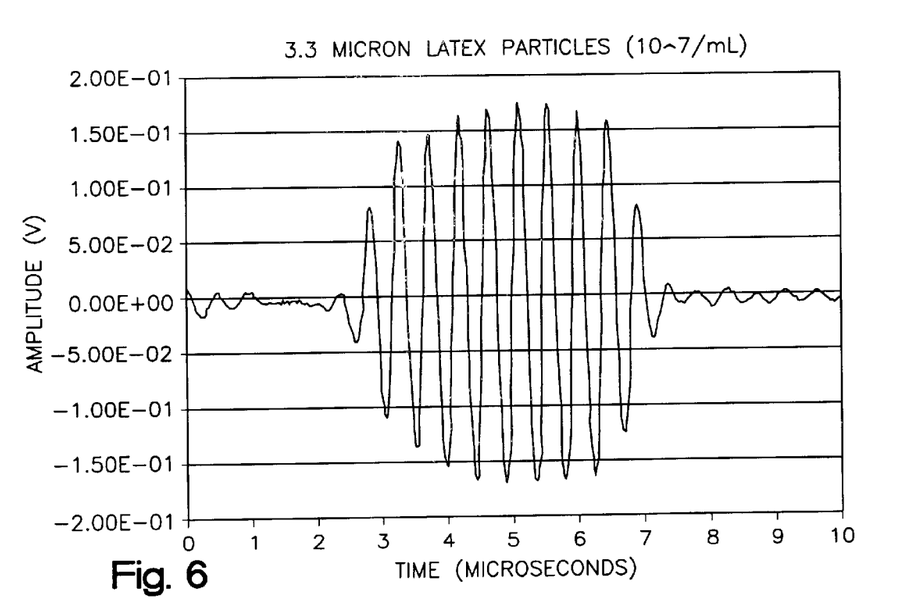
Figure 7:
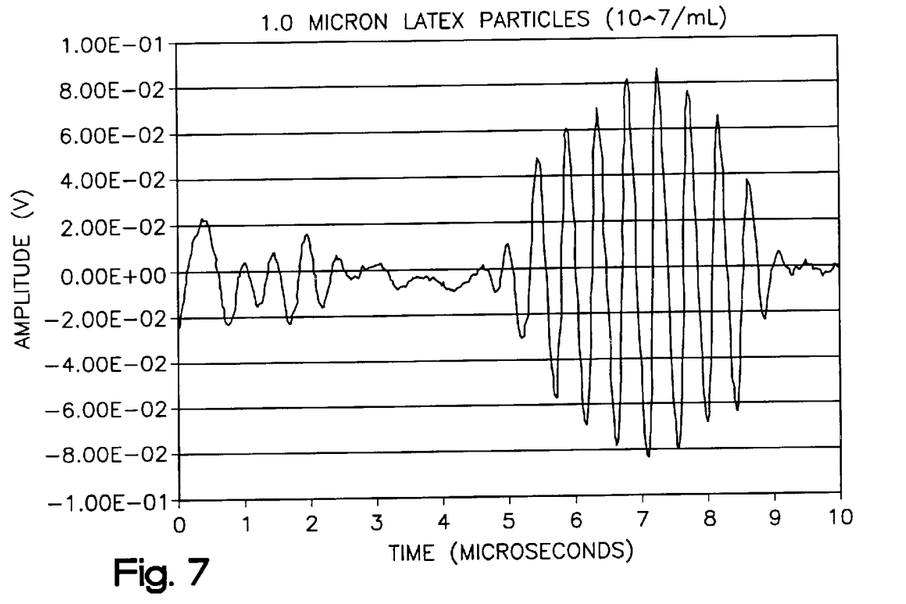

FIG. 6 represents data corresponding to FIG. 5, but in this particular case the particulate has a diameter of 3.3 micron at the same concentration. In this case, the amplitude of the received signal for a given event is approximately $1.70 \times 10^{-1}$ volts. FIG. 7 represents similar data except that the particles have a diameter of 1.0 micron. In this case, the amplitude of the received signal for a given event is approximately $8 \times 10^{-2}$ volts. Thus, for a given event captured by the circuit 52 in the signal received by the transmitter/receiver unit 38, it is shown that the amplitude of the event is related to the size of the wear debris particles. The circuit 52 together with the data processing circuit 60 may be programmed and/or configured using conventional techniques to capture and analyze the signal received by the transmitter/receiver unit 38 in order to evaluate the amplitude of the signal for each of the events contained in the received signal, as will be appreciated. The data processing circuit 60 automatically evaluates the amplitude of the events in order to determine the respective sizes of the wear debris particles.

Figure 8:
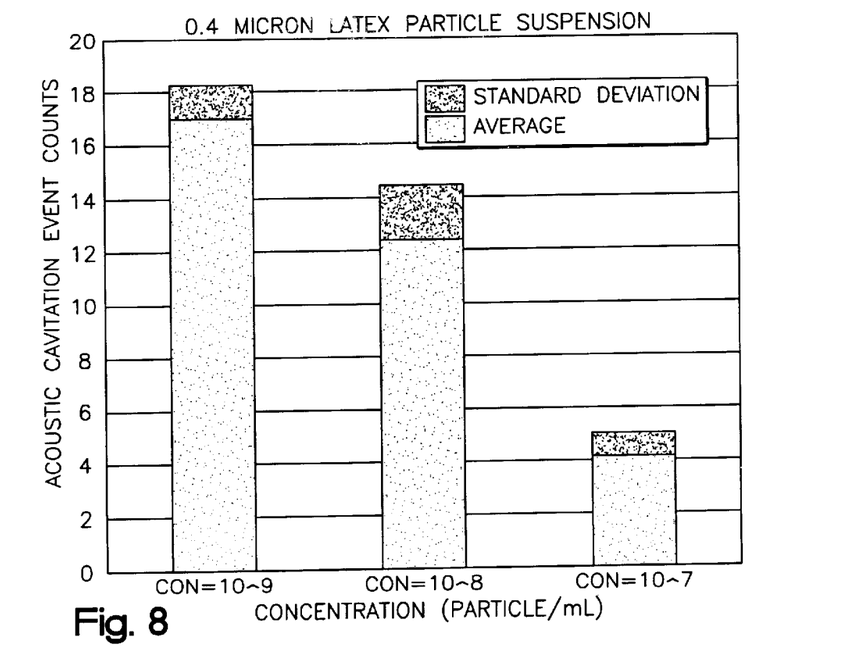
FIGS. 8 and 9 represent data indicative of the manner in which the number of cavitation events corresponds to particle concentration in accordance with the present invention.
Figure 9:
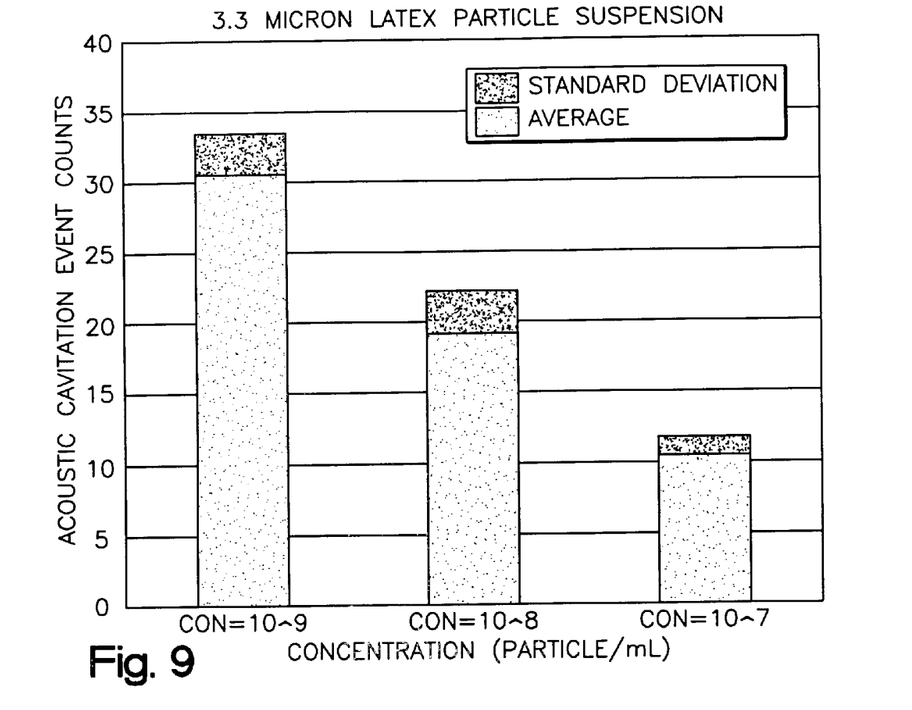

FIG. 8 is a data histogram representing the number of events which are detected in the acoustic response signal received by the transmitter/receiver unit 38 following an acoustic excitation pulse, as a function of the concentration of particles. As is shown in FIG. 8, for particles having a diameter of 0.4 micron the number of events in the received signal tracks the concentration of particles in the fluid. In other words, the higher the concentration of particles the higher the number of events which are detected. FIG. 9 shows a similar correspondence between the concentration of particles and the number of events which are detected following an excitation pulse for particles having a diameter of 3.3 microns.

The data processing circuit 60 is programmed and/or configured using conventional techniques to analyze the signal received by the transmitter/receiver unit 38 in order to evaluate the number of events contained in the received signal for the different sized particles. The data processing circuit 60 can then automatically reach a determination as to the concentration of the respective sized particles.

Advanced signal processing methods such as neural networks, expert systems, digital transforms, etc. may be applied by the data processing circuit 60 in order to increase resolution of the apparatus in distinguishing between the different particle sizes and concentrations, as will be appreciated.

Figure 10:
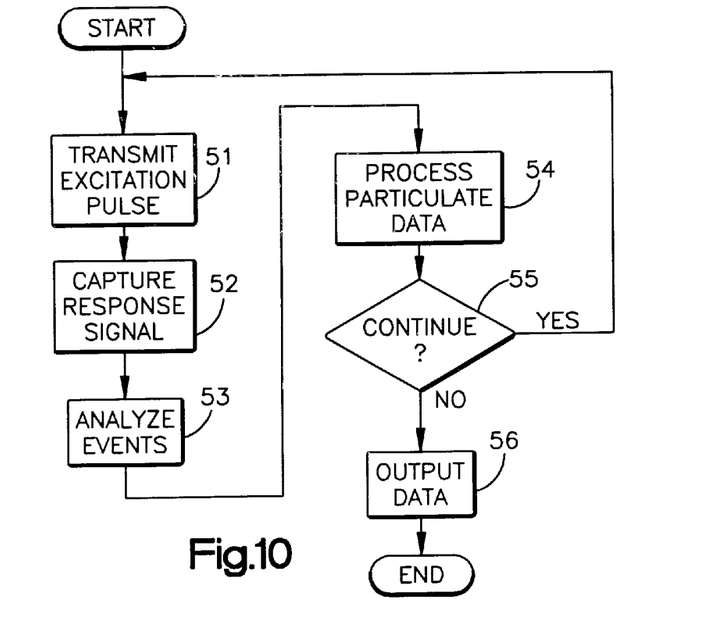
FIG. 10 is a flowchart representing the operation of the system for detecting wear debris particulate in accordance with the present invention.

FIG. 10 represents the operation of the system 30 in accordance with the present invention. As shown in step S1, the acoustic analyzer 36 (FIG. 4) transmits an acoustic (e.g., ultrasonic) energy pulse via the transmitter/receiver unit 38 towards the medical implant 32 and the region believed to contain wear debris particulate. In step S2, the acoustic analyzer receives the acoustic energy scattered back from the particulate via the transmitter/receiver unit 38. The signal conditioning circuit 58 conditions the received signal and the data processing circuit 60 stores the received signal.

The data processing circuit 60 in step S3 then analyzes the received signal. For example, the received signal is processed to identify the different cavitation events which occur amongst the wear debris particulate in the fluid surrounding the joint. The amplitude of each event and number of events of each amplitude are then determined by the control circuit 52 in step S3. The data processing circuit 60 compares the amplitude of each event with predetermined values stored in a look up table in memory, for example, in order to ascertain the size of the particles. In addition, the data processing circuit 60 counts the number of events of each amplitude and refers to a set of predetermined values stored in a look up table in memory to ascertain a corresponding concentration of particles. Alternatively, the data processing circuit 60 may employ a neural network or other advanced signal processing in order to evaluate the different events in order to ascertain particle size, concentration, etc.

Next, in step S4 the data processing circuit 60 processes the particulate data in order to produce an output such as the particle size and/or concentration as determined in step S3. In the case of performing several excitation pulses in step S1, the data processing circuit 60 in step S4 may average or apply statistical methods to the particulate data obtained in response to each excitation pulse in order to produce an output.

In step S5, the data processing circuit 60 determines if the detection process is to continue (e.g., based on an operator input). If so, the process returns to step S1. Otherwise, the data processing circuit 60 outputs the data (e.g., the detected particle size(s) and/or concentration(s) in step S6 and the process is completed.

Accordingly, the inventors have developed a manner for non-invasively detecting and analyzing wear debris particulate associated with a medical implant.

Moreover, the invention has utility in that it also may be used to monitor and characterize wear debris generated by medical implants in a simulation environment. For example, the present invention may be used to characterize wear debris generated by an artificial joint using a joint motion simulation device. The artificial joint is enclosed in a sack filled with saline or some other fluid to emulate an actual joint with a body, for example. The artificial joint is cycled according to a desired time period and/or number of repetitions. The joint is then analyzed using the above procedures in order to gain information on the various types, sizes and responses of the wear debris particulate occurring over time, e.g., with respect to different implant devices, etc.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A method of detecting wear debris particulate from a medical implant within a body of a living animal, comprising the steps of:
   transmitting acoustic energy from outside to the body to a soft tissue region proximate the medical implant generating wear debris particles;
   using a receiver located outside the body to detect resultant acoustic energy generated by the wear debris particles and produce a receive signal indicative thereof;
   processing the receive signal to evaluate at least one parameter associated with the wear debris particles; and
   providing an output indicative of the at least one parameter.

2. The method of claim 1, wherein the at least one parameter comprises size of the wear debris particles.

3. The method of claim 1, wherein the at least one parameter comprises concentration of the wear debris particles.

4. The method of claim 1, wherein the acoustic energy generated by the wear debris particles is a result of at least one type of cavitation occurring among the particles.

5. The method of claim 1, wherein the receive signal is detected and electronically captured.

6. The method of claim 1, wherein the receive signal is processed by evaluating different events captured in the receive signal.

7. The method of claim 6, wherein an amplitude of an event is processed to determine a size of the wear debris particles.

8. The method of claim 7, wherein the size of the wear debris particles is determined by referring to a look up table using the amplitude as an index.

9. The method of claim 6, wherein a frequency of events is processed to determine a concentration of the wear debris particles.

10. The method of claim 9, wherein the concentration of the wear debris particles is determined by referring to a look up table using the frequency of events as an index.

11. The method of claim 1, wherein the output is the size of the wear debris particles.

12. The method of claim 1, wherein the output is the concentration of the wear debris particles.

13. The method of claim 1, wherein the output is produced on a display.

14. The method of claim 1, wherein the output is provided onto a local area network or submitted to a database system via the Internet.

15. The method of claim 1, wherein the medical implant is an artificial joint.

16. The method of claim 15, wherein the artificial joint is a hip joint.

17. The method of claim 15, wherein the artificial joint is a knee joint.

18. The method of claim 15, wherein the artificial joint is a shoulder joint.

19. An apparatus for detecting wear debris particulate from a medical implant within a body of a living animal, comprising:
   an acoustic transmitter for transmitting acoustic energy from outside to body to a soft tissue region proximate the medical implant generating wear debris particles;
   an acoustic receiver located outside the body to detect resultant acoustic energy generated by the wear debris particles and produce a receive signal indicative thereof;
   a processor for processing the receive signal to evaluate at least one parameter associated with the wear debris particles; and
   an output for indicating the at least one parameter.

20. The apparatus of claim 19, wherein the at least one parameter comprises size of the wear debris particles.

21. The apparatus of claim 19, wherein the at least one parameter comprises concentration of the wear debris particles.

22. The apparatus of claim 19, wherein the acoustic energy scattered by the wear debris particles is a result of cavitation occurring among the particles.

23. The apparatus of claim 19, wherein the receive signal is detected and electronically captured.

24. The apparatus of claim 19, wherein the receive signal is processed by evaluating different events captured in the received signal.

25. The apparatus of claim 24, wherein an amplitude of an event is processed to determine a size of the wear debris particles.

26. The apparatus of claim 25, wherein the size of the wear debris particles is determined by referring to a look up table using the amplitude as an index.

27. The apparatus of claim 24, wherein a frequency of events is processed to determine a concentration of the wear debris particles.

28. The apparatus of claim 27, wherein the concentration of the wear debris particles is determined by referring to a look up table using the frequency of events as an index.

29. The apparatus of claim 19, wherein the output is the size of the wear debris particles.

30. The apparatus of claim 19, wherein the output is the concentration of the wear debris particles.

31. The apparatus of claim 19, wherein the output is produced on a display.

32. The apparatus of claim 19, wherein the output is provided onto a local area network or submitted to a database system via the Internet.

33. The apparatus of claim 19, wherein the medical implant is an artificial joint.

34. The apparatus of claim 33, wherein the artificial joint is a hip joint.

35. The apparatus of claim 33, wherein the artificial joint is a knee joint.

36. The apparatus of claim 33, wherein the artificial joint is a shoulder joint.

37. A method of characterizing wear debris particulate from a medical implant within a body of a living animal, comprising the steps of:

configuring the medical implant in an environment designed to simulate conditions incurred by the medical implant within the body of the living animal;

transmitting acoustic energy toward the medical implant;

using a receiver to detect resultant acoustic energy generated by wear debris particles produced by the medical implant and produce a receive signal indicative thereof; and processing the receive signal to characterize at least one parameter associated with the wear debris particles.

* * * * *